(12) United States Patent
Trapp et al.

(10) Patent No.: US 11,376,127 B2
(45) Date of Patent: Jul. 5, 2022

(54) ARTIFICIAL CHORDAE TENDINEAE REPAIR DEVICES AND DELIVERY THEREOF

(71) Applicant: W. L. Gore & Associates, Inc., Newark, DE (US)

(72) Inventors: Benjamin M. Trapp, Flagstaff, AZ (US); James L. Goepfrich, Flagstaff, AZ (US); Brandon C. Hedberg, Flagstaff, AZ (US); Edward E. Shaw, Flagstaff, AZ (US); Jason D. Hemmer, Newark, DE (US); Paul D. Goodman, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 90 days.

(21) Appl. No.: 16/226,002

(22) Filed: Dec. 19, 2018

(65) Prior Publication Data

US 2019/0183648 A1   Jun. 20, 2019

Related U.S. Application Data

(60) Provisional application No. 62/608,356, filed on Dec. 20, 2017.

(51) Int. Cl.
*A61F 2/24*   (2006.01)

(52) U.S. Cl.
CPC .......... *A61F 2/2466* (2013.01); *A61F 2/2457* (2013.01); *A61F 2/2463* (2013.01); *A61F 2220/0008* (2013.01)

(58) Field of Classification Search
CPC .... A61F 2/2466; A61F 2/2457; A61F 2/2454; A61F 2/2427; A61F 2/848;
(Continued)

(56) References Cited

U.S. PATENT DOCUMENTS 7,635,386 B1   12/2009   Gammie
8,147,542 B2   4/2012   Maisano
(Continued)

FOREIGN PATENT DOCUMENTS

CH   WO2017066890   *   4/2017   ............... A61F 2/24
JP   2014-523256 A   9/2014
(Continued)

OTHER PUBLICATIONS

International Search Report and Written Opinion from PCT/US2018/066747, dated Mar. 25, 2019, 15 pages.
(Continued)

*Primary Examiner* — Kathleen S Holwerda
*Assistant Examiner* — Uyen N Vo

(57) ABSTRACT

Various aspects of the present disclosure are directed toward apparatuses, systems, and methods that include device for chordae tendineae repair. The device may include a flexible cord having a first end and a second end; and a helical wire configured to attach to one of the first end and the second end of the flexible cord and anchor the flexible cord to a leaflet of a heart valve; and a capture device having a channel and configured to clamp the leaflet of the heart valve and deliver the flexible cord through the channel to anchor the helical wire to the leaflet.

12 Claims, 17 Drawing Sheets

(58) Field of Classification Search
CPC ...... A61F 2002/8483; A61F 2002/8486; A61F 2220/0008
See application file for complete search history.

(56) References Cited

U.S. PATENT DOCUMENTS

| | | | |
|---|---|---|---|
| 9,877,833 B1 * | 1/2018 | Bishop | A61F 2/2457 |
| 2007/0118151 A1 * | 5/2007 | Davidson | A61B 17/0469 606/144 |
| 2008/0125860 A1 | 5/2008 | Webler et al. | |
| 2011/0011917 A1 * | 1/2011 | Loulmet | A61F 2/2457 227/181.1 |
| 2014/0031926 A1 | 1/2014 | Kudlik et al. | |
| 2014/0046347 A1 | 2/2014 | Cully | |
| 2014/0142610 A1 * | 5/2014 | Larsen | A61B 17/0057 606/200 |
| 2015/0164637 A1 * | 6/2015 | Khairkhahan | A61L 27/3625 623/2.17 |
| 2016/0008132 A1 * | 1/2016 | Cabiri | A61F 2/2442 623/2.11 |
| 2017/0156861 A1 | 6/2017 | Longoria et al. | |
| 2017/0202669 A1 * | 7/2017 | Schaffner | A61F 2/2418 |
| 2017/0252032 A1 | 9/2017 | Hiorth | |
| 2017/0304050 A1 | 10/2017 | Keidar et al. | |
| 2017/0319333 A1 | 11/2017 | Tegels | |
| 2018/0235758 A1 | 8/2018 | Biadillah et al. | |
| 2018/0303614 A1 | 10/2018 | Schaffner et al. | |
| 2019/0175346 A1 | 6/2019 | Schaffner et al. | |

FOREIGN PATENT DOCUMENTS

| | | | | |
|---|---|---|---|---|
| JP | 2015-523898 A | 8/2015 | | |
| JP | 2018-531093 A | 10/2018 | | |
| JP | 2018-533398 A | 11/2018 | | |
| JP | 2019-513026 A | 5/2019 | | |
| WO | WO-2012040865 A1 * | 4/2012 | ........... | A61F 2/2457 |
| WO | WO-2012137208 A1 | 10/2012 | | |
| WO | 2013/192107 A1 | 12/2013 | | |
| WO | WO-2017066889 A1 | 4/2017 | | |
| WO | WO-2017066890 A1 * | 4/2017 | ......... | A61B 17/0401 |
| WO | 2017/072229 A1 | 5/2017 | | |
| WO | WO-2017079153 A1 | 5/2017 | | |

OTHER PUBLICATIONS

International Preliminary Report on Patentability received for PCT Patent Application No. PCT/US2018/066747, dated Jul. 2, 2020, 9 pages.

* cited by examiner

ARTIFICIAL CHORDAE TENDINEAE REPAIR DEVICES AND DELIVERY THEREOF

CROSS-REFERENCE TO RELATED APPLICATION

This application claims the benefit of Provisional Application No. 62/608,356, filed Dec. 20, 2017, which is incorporated herein by reference in its entirety for all purposes.

FIELD

The present disclosure relates generally to transseptal artificial chordae tendineae implantation devices, apparatuses, systems and methods.

BACKGROUND

Leaflets of atrioventricular valves (mitral and tricuspid) are thin, diaphanous structures that rely on a system of long, thin, cord-like supports to maintain competence of the valve in the loaded condition. These supports, chordae tendineae, attach the papillary muscles to the valve leaflets.

Chordae tendineae can degenerate and stretch, which can result in leaflet prolapse. As a result, the leaflet(s) can misalign under systolic loading. An open surgical procedure for chordae tendineae is highly invasive and carries with it a high morbidity and mortality risk. Thus, delivery and implantation of artificial chordae tendineae(s) in chordae tendineae replacement or repair without using an open surgical procedure (or a transapical or transatrial delivery approach) can reduce morbidity and mortality risk.

SUMMARY

According to one example ("Example 1"), a device for chordae tendineae repair, the device including: a flexible cord having a first end and a second end; and a helical wire configured to attach to one of the first end and the second end of the flexible cord and anchor the flexible cord to a leaflet of a heart valve; and a capture device having a channel and configured to clamp the leaflet of the heart valve and deliver the flexible cord through the channel to anchor the helical wire to the leaflet.

According to another example ("Example 2") further to Example 1, further including a puncture needle, and the capture device includes a channel configured to pass the puncture needle and the flexible cord therethrough, and the puncture needle is configured to puncture the leaflet while the capture device clamps the leaflet.

According to another example ("Example 3") further to Example 2, the puncture needle includes a lumen configured to pass the flexible cord therethrough.

According to another example ("Example 4") further to any one of Examples 1-3, further including an anchor configured to anchor the flexible cord in a tissue wall of a patient's heart.

According to another example ("Example 5") further to any one of Examples 1-4, the capture device includes a hinge configured to open and close the capture device.

According to another example ("Example 6") further to any one of Examples 1-5, further including a suction device configured to capture the leaflet for arrangement of the flexible cord through the leaflet.

According to one example ("Example 7"), a method for chordae tendineae repair, the method including: capturing a leaflet of a heart valve of a patient using a capture device; arranging a flexible cord through the leaflet while the leaflet is captured by the capture device; anchoring a first end of the flexible cord within the leaflet using a helical wire; and anchoring a second end of the flexible cord within a tissue wall of a heart of the patient.

According to another example ("Example 8"), further to Example 7, the tissue wall is a papillary muscle of a left ventricular wall of the patient, and the anchoring the second end of the flexible cord occurs prior to anchoring the first end of the flexible cord.

According to another example ("Example 9") further to any one of Examples 7-8, anchoring the second end of the flexible cord includes penetrating the tissue wall with a puncture needle for insertion of an anchor coupled to the second end of the flexible cord.

According to another example ("Example 10"), further to Example 9, the capture device includes a channel configured to pass the puncture needle and the flexible cord and the puncture needle includes a lumen configured to pass the flexible cord therethrough.

According to another example ("Example 11") further to any one of Examples 7-10, the capture device includes a hinge configured to open and close the capture device.

According to another example ("Example 12"), a chordae tendineae repair device includes: a flexible cord having a first end and a second end; and an anchor configured to attach to one of the first end and the second end of the flexible cord and anchor the flexible cord to a leaflet of a heart valve or to a tissue wall of the heart.

According to another example ("Example 13"), further to Example 12, the anchor is a helical wire and is wrapped with a film.

According to another example ("Example 14"), further to any one of Examples 12 or 13, the anchor is configured to protect or fill a puncture in the leaflet of the heart valve through which the anchor is arranged.

According to another example ("Example 15"), further to Example 12, further including a second anchor arranged at the second end of the flexible cord and the anchor is arranged at the first end of the flexible cord, and the first anchor and the second anchor penetrate the tissue wall without being anchored in the leaflet.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Figure 1:
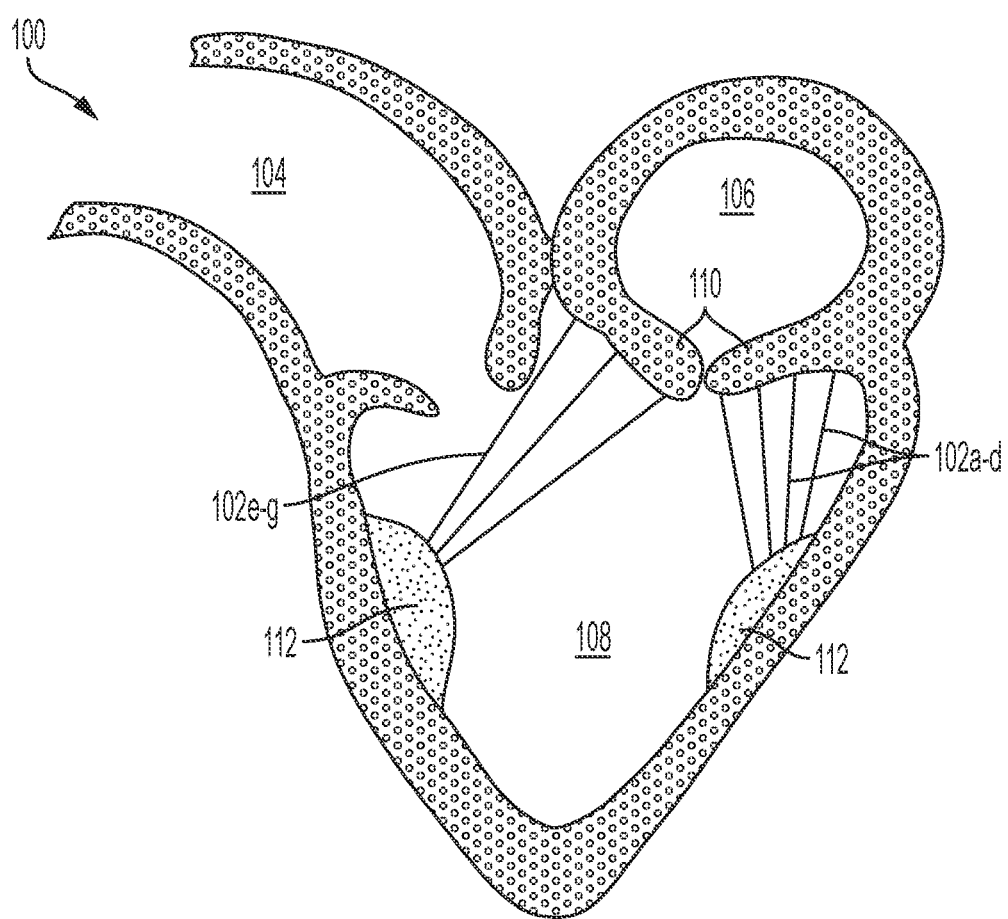
FIG. 1 is an illustration of a patient's heart and chorda tendineae in accordance with an embodiment.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

The chordae tendineae repair (or replacement) devices, methods, and systems discussed herein are generally directed toward an artificial chordae that includes a flexible cord, which is biocompatible and may be made of polypropylene, Nylon (polyamide), polyester, polyvinylidene fluoride or polyvinylidene difluoride (PVDF), silk, or formed of a fluoropolymer, including without limitation, polytetrafluoroethylene (PTFE) or expanded polytetrafluoroethylene (ePTFE). The flexible cord may be attached to the valve leaflet. The flexible cord may be sutures which can also be divided into two types on the basis of material structure (i.e. monofilament sutures and multifilament or braided sutures). The valve may be the mitral valve or tricuspid valve, for example, with the flexible cord being attached at the superior end to the leaflet and to the papillary or ventricular wall at the inferior end. One or both ends of the flexible cord may include an anchor. In certain instances, the inferior end of the flexible cord is attached to a self-expanding (e.g., nitinol (NiTi)) anchor which is in turn attached to the papillary or ventricular wall. The anchor may be shaped set NiTi with several leg members that are displaced from a central tube to resist motion. Anchors are shown in, for example, FIG. 3, FIG. 6, FIG. 13, FIG. 14, and FIG. 17. For further discussion of the anchors, reference may be made to U.S. Patent Publication No. 2014/0046347, which is incorporated herein by reference in its entirety for the specific purposes of teaching anchors for engaging tissue.

Various aspects of the present disclosure are also directed toward transcatheter, transseptal chordal repair (or replacement) treatment. Delivery of the artificial chordae can also be done with surgical intervention. Transcatheter delivery is less invasive than an open surgical procedures or transapical or transatrial approaches. The delivery devices, methods, and systems discussed herein are less invasive and have reduced morbidity and mortality risk compared to open surgical and transapical or transatrial delivery approaches.

FIG. 1 is an illustration of a patient's heart 100 and chorda tendineae 102a-g in accordance with an embodiment. FIG. 1 shows the left side of the patient's heart 100 which includes the aortic arch 104, left atrium 106, left ventricle 108, with the mitral valve located between the left atrium 106 and the left ventricle 108. The chordae tendineae 102a-g are attached to the leaflets 110 of the mitral valve on one end, and papillary muscles 112 in the left ventricle 108 on the other end.

Stretched, ruptured, or broken chordae tendineae 102a-g may alter functionality of the leaflets 110 of the mitral valve. In these instances, for example, the mitral valve may no longer fully coapt or close. As a result, blood can flow from the left ventricle 108 back into the left atrium 106 (e.g., mitral regurgitation).

Figure 2:
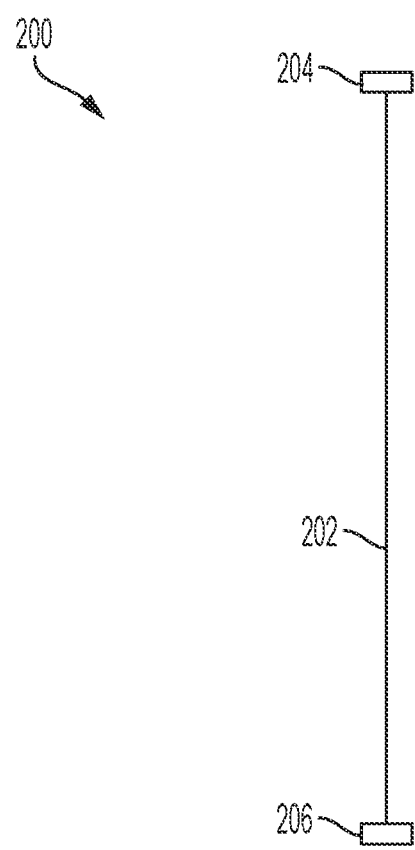
FIG. 2 is an illustration of an example chordae tendineae repair device in accordance with an embodiment.

FIG. 2 is an illustration of an example chordae tendineae repair device 200 in accordance with an embodiment. In certain instances, the chordae tendineae repair (or replacement) device 200 may include a flexible cord 202, a first attachment member 204 arranged at one end of the flexible cord 202, and a second attachment member 206 arranged at the other end of the flexible cord 202. In certain embodiments, the flexible cord 202 (e.g., tissue connector) includes an elongate body. In some embodiments, the flexible cord can be porous. The material of the flexible cord 202 may include a fluoropolymer, including without limitation, PTFE and/or ePTFE, nylon, polypropylene, polyester, PVDF, silk, or other similar materials. One embodiment of a fluoropolymer based suture, GORE-TEX® Sutures for Chordae Tendineae ("CT") Repair or Replacement, is currently on market to be used for mitral valve prolapse. The suture is additionally supplied with fluoropolymer (e.g., ePTFE) pledgets. The pledgets provided with GORE-TEX® Sutures for Chordae Tendineae ("CT") Repair or Replacement are supplied with pre-punched holes. Other PTFE pledgets are sold by several companies and are commonly used to support sutures where there is a possibility of the suture tearing through friable tissue. The suture thread is a permanent medical device implant for a single use. GORE-TEX® Sutures for Chordae Tendineae ("CT") Repair are considered to be a "gold standard" suture for CT Repair procedures.

The first attachment member 204 and the second attachment member 206 are configured to attach the flexible cord 202 tissue of the heart. The first attachment member 204 and the second attachment member 206 may be anchors that pierce the tissue and retain the flexible cord 202 between a first location and a second location with the first attachment member 204 and the second attachment member 206 piercing and retaining at a surface of or within the tissue at, respectively, the first location and the second location. The first attachment member 204 and the second attachment member 206 may be barbs, fixation helixes, or any similar structure.

In certain instances, the flexible cord 202 may be used for treating a defective mitral or tricuspid valve. In these such instances, an apical region of a heart is percutaneously accessed with a catheter-based device. The cardiac valve is repaired by replacing at least one chordae tendineae (e.g., as shown in FIG. 1). The replaced chordae tendineae may include the flexible cord 202, which can also be referred to as a tissue connector due to the flexible cord 202 connecting two portions of the heart tissue. In other instances, the flexible cord 202 may be wrapped about a circumference of the heart or valve annulus may be arranged within a leaflet or tissue. In certain instances, the helical wire 300 may be flat to ensure closure of a valve that is experiencing regurgitation. In these instances, the flexible cord 202 slightly compresses the heart to ensure that the leaflets of the valve fully close.

Figure 3:
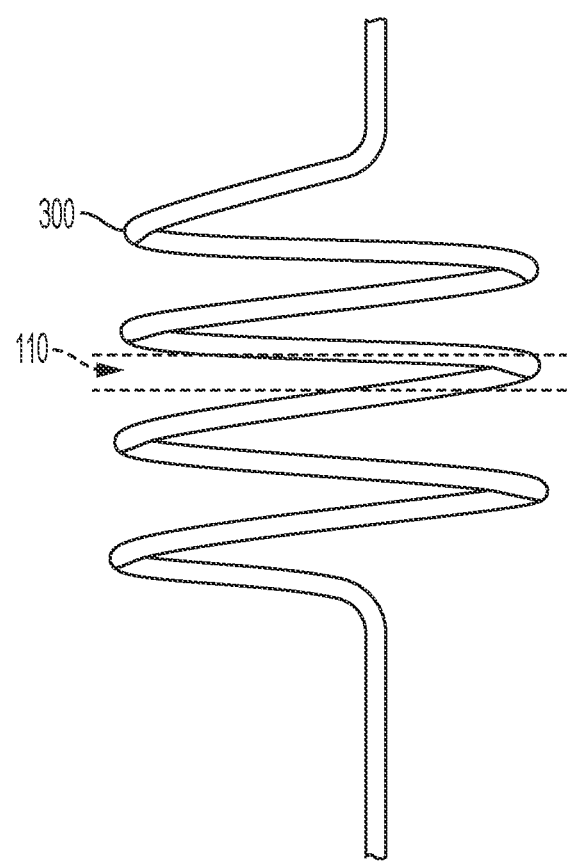
FIG. 3 shows an example component of a chordae tendineae repair device in accordance with an embodiment.

FIG. 3 shows an example component of a chordae tendineae repair device in accordance with an embodiment. The chordae tendineae repair (or replacement) device component, shown in FIG. 3, is a helical wire 300. The helical wire 300 is configured to be attached to an end (a first and/or second end) of a flexible cord, as shown in FIG. 2 and FIGS. 6-10, that may anchor to a leaflet 110 of a heart valve of a patient. The helical wire 300 may be screwed, twisted, or wrenched into the leaflet 110. In addition, the helical wire 300 may be delivered in constrained state and allowed to expand with an expanded coil portion on either side of a leaflet. As a result, the helical wire 300 couples or anchors the flexible cord to the leaflet 110 at one end of the flexible cord.

In certain instances, the helical wire 300 may be metallic (e.g., nitinol (NiTi)) and wrapped with ePTFE. In addition, the helical wire 300 may be configured to protect or fill a puncture in the leaflet 110 of the heart valve through which the screw is arranged. In this manner, the helical wire 300 anchors the flexible cord to the leaflet 110 and also functions as a pledget stopping or filling the opening through which the helical wire 300 is arranged. The helical wire 300, and the flexible cord to which the helical wire 300 is coupled, may be used for valve prolapse (e.g., mitral valve leaflet prolapse) or leaflet 110 flailing due to degenerative mitral regurgitation.

The helical wire 300, in certain instances, adjusts the tension of the flexible cord in chordae tendineae repair. The depth at which the helical wire 300 is screwed, twisted, or penetrated into the leaflet 110, adjusts the tension on the flexible cord to which the helical wire 300 is attached. This allows the helical wire 300 and the flexible cord to adjust to the amount of tension needed to treat mitral valve leaflet prolapse or leaflet 110 flailing such that the leaflet 110 opens and closes at the desired and natural effect.

The helical wire 300 may have one or more coils, as is shown. The number of turns or coils of the helical wire 300 can be varied in order to lengthen or shorten the depth at which the helical wire 300 may be arranged within a leaflet or tissue. In certain instances, the helical wire 300 may have a flat or low profile end portion configured to conform to an upper or top side of the leaflet with the flexible cord being arranged through the upper or top side of the leaflet and passed through a lower or bottom side of the leaflet toward heart tissue.

Figure 4:
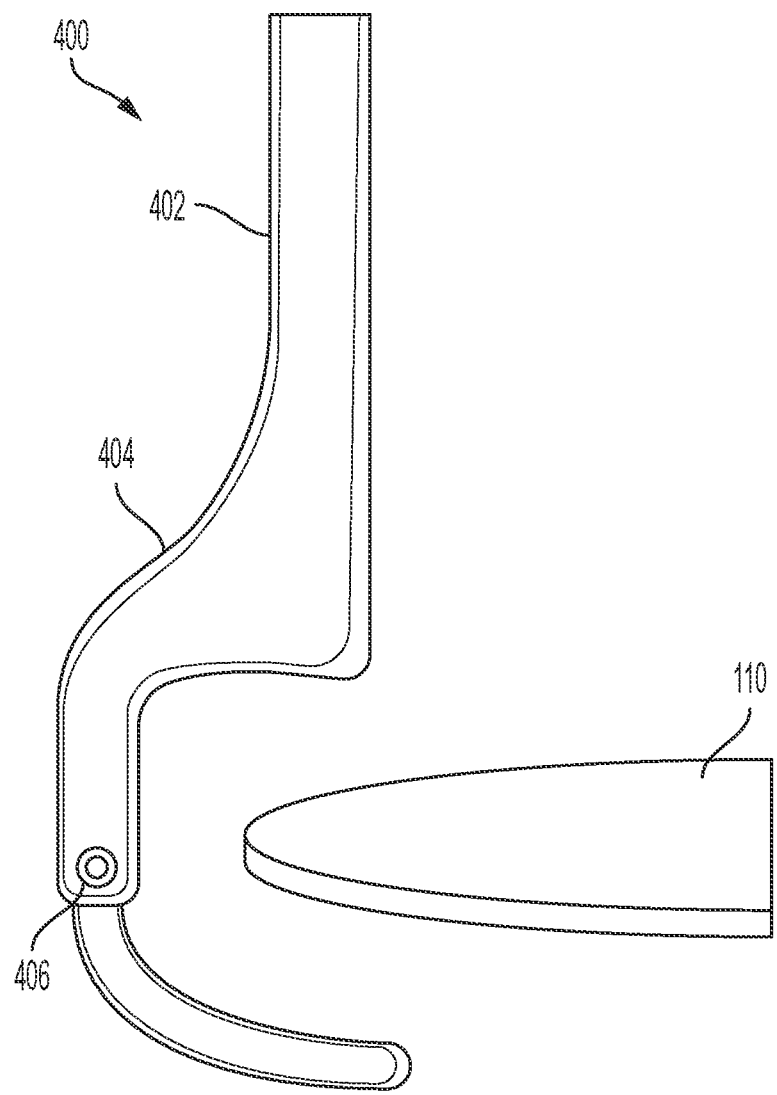
FIG. 4 shows an example component of a chordae tendineae repair device in a first configuration in accordance with an embodiment.

FIG. 4 shows an example component of a chordae tendineae repair device in a first configuration in accordance with an embodiment. The chordae tendineae repair (or replacement) device shown in FIG. 4 is a delivery device 400 that may include a catheter 402 and a capture device 404. The capture device 404 is configured to clamp a leaflet 110 of a heart valve for repair of chordae tendineae. In certain instances, the capture device 404 may clamp, hold, or grasp the leaflet 110 to facilitate delivery of a flexible cord through the leaflet 110 for the chordae tendineae repair.

In certain instances, the delivery device 400 may be used for transcatheter delivery of a chordae tendineae repair device. The capture device 404 may be arranged at a distal end of the catheter 402 as shown in FIG. 4. The capture device 404 is shown in a closed (clamping) configuration in FIG. 4. The capture device 404 may include a hinged portion 406 to facilitate movement of the capture device 404 between open and closed (clamping) position.

Figure 5:
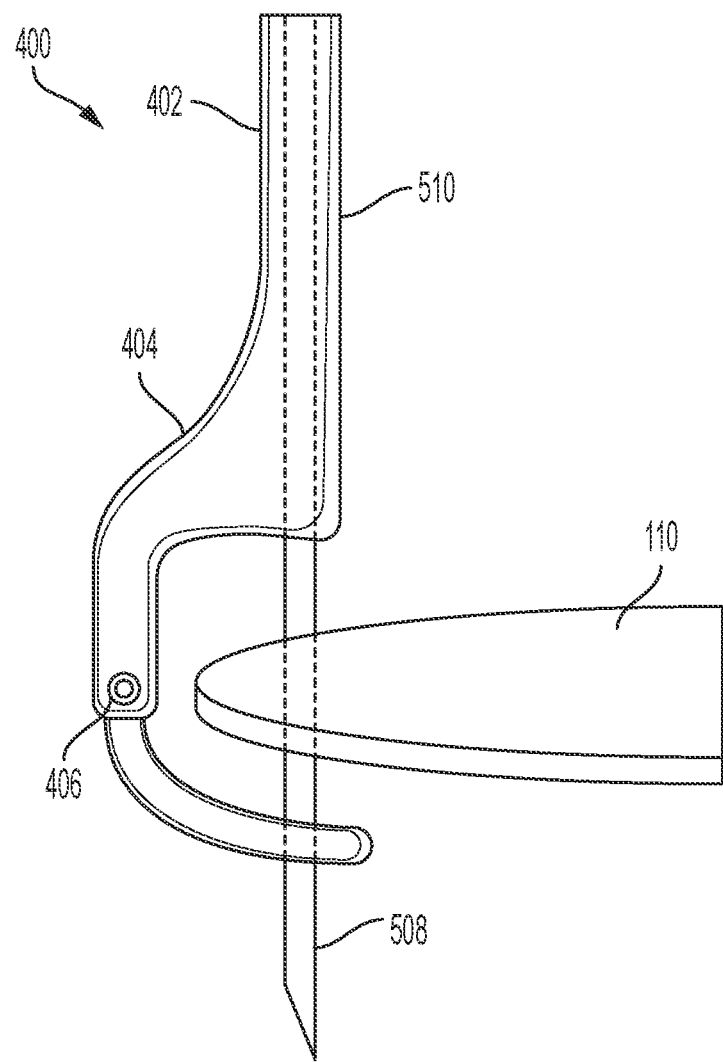
FIG. 5 shows an example component of a chordae tendineae repair device in a second configuration in accordance with an embodiment.

FIG. 5 shows an example chordae tendineae repair device in a second configuration in accordance with an embodiment. As shown in FIG. 5, a delivery device 400 is shown with a capture device 404 having captured and clamped onto a leaflet 110. In certain instances, the delivery device 400 also includes a needle 508.

The needle 508 may be arranged through a channel 510 in a catheter 402 of the delivery device. The channel 510, in certain instances, is also through the capture device 404. When the capture device 404 clamps onto the leaflet 110, the leaflet 110 may be stabilized and properly aligned for the needle 508 to create an opening in the leaflet 110. The needle 508 passes through the created opening in the leaflet 110 and may be arranged to contact a tissue wall of the heart. As shown in FIG. 5, the needle 508 is arranged through the channel 510 and through both portions of the capture device 404. In certain instances, the capture device 404 includes multiple portions that are separated by a hinged portion 406 that facilitates movement of the capture device 404 between open and closed (clamping) position.

Figure 6:
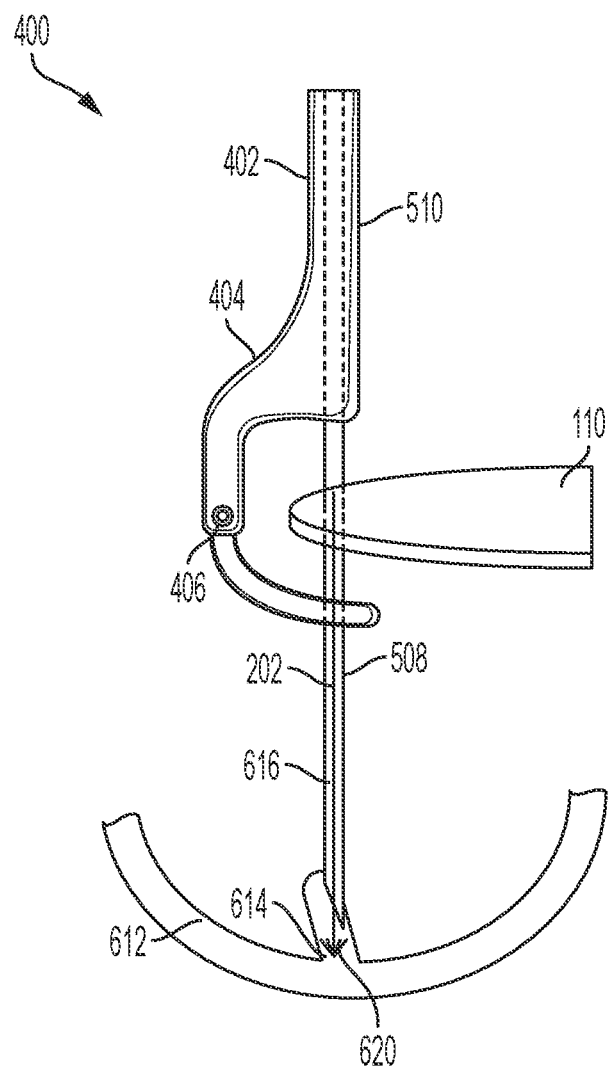
FIG. 6 shows an example chordae tendineae repair device in a third configuration in accordance with an embodiment.

FIG. 6 shows an example chordae tendineae repair device in a third configuration in accordance with an embodiment. As shown in FIG. 6, a delivery device 400 is shown with a capture device 404 having captured and clamped onto a leaflet 110. In addition, the delivery device 400 is in a configuration such that a needle 508 has been passed through the leaflet 110 and into a tissue wall 612 of a patient's heart. In certain instances, the tissue wall 612 may be a left ventricle of a patient, and, more specifically, the tissue wall 612 may be a papillary muscle 614 in the left ventricle.

In certain instances, the needle 508 includes a lumen 616. As shown in FIG. 6, a flexible cord 202 is arranged through the lumen 616. The lumen 616 of the needle 508 may be configured to pass the flexible cord 202 through the lumen 616 for chordae tendineae repair (or replacement). The flexible cord 202 may be an artificial chordae tendineae as discussed above with reference to FIGS. 1-2. The flexible cord 202 may include an anchor 620 at one end to anchor the flexible cord 202 in the tissue wall 612. The anchor 620 may have multiple leg members, a helical wire (e.g., similar to helical wire 300), a spur or another similar structure.

In instances where the anchor 620 includes multiple leg members, as shown in FIG. 6, the leg members expand and are pushed into the tissue wall 612 by the needle 508 or a push rod (not shown) arranged through the lumen 616 of the needle 508. The anchor 620 may be a NiTi (nickel-titanium alloy) shape set anchor that is covered in at least part (e.g., wrapped) in a fluoropolymer such as ePTFE. In certain instances and as shown, the needle 508 may include a surface that is shaped to assist puncturing.

Figure 7:
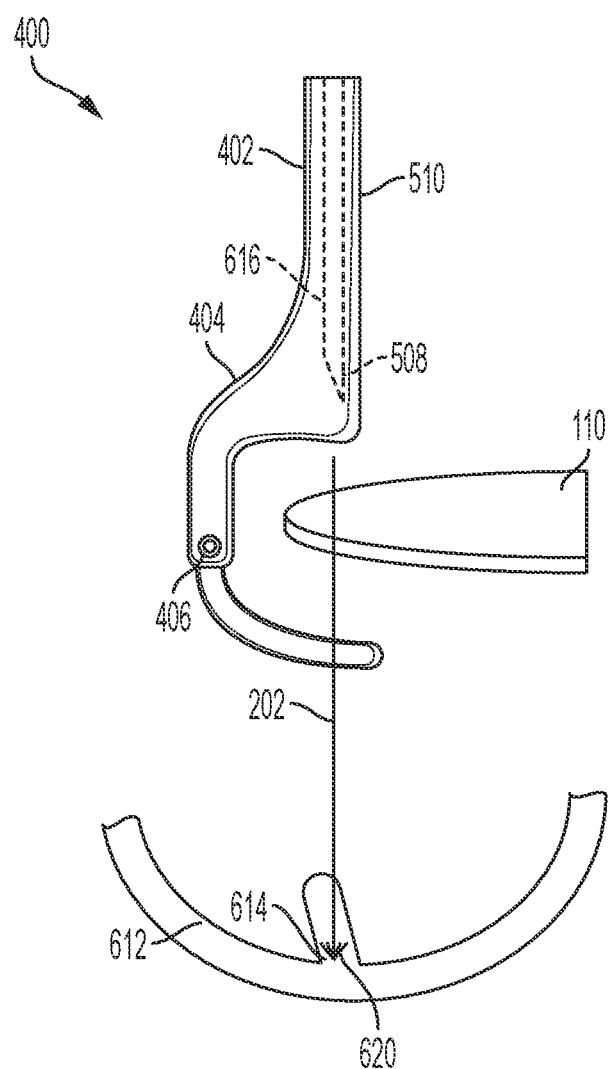
FIG. 7 shows an example chordae tendineae repair device in a fourth configuration in accordance with an embodiment.

After the leaflet 110 is captured by the capture device 404 and the needle 508 is advanced through the channel 510, through the leaflet 110 and into the tissue wall 612 with the anchor 620, the flexible cord 202 is anchored at one end. The needle 508 may be retracted through the channel 510 as shown in FIG. 7. In certain instances, tension on the flexible cord 202 may be increased by embedding the anchor 620 further into the tissue wall 612 or lessened by decreasing the depth at which the anchor 620 is embedded in the tissue wall 612. The anchor 620 may be embedded at any location along the tissue wall 612 including the papillary muscle 614, as discussed above.

Figure 8:
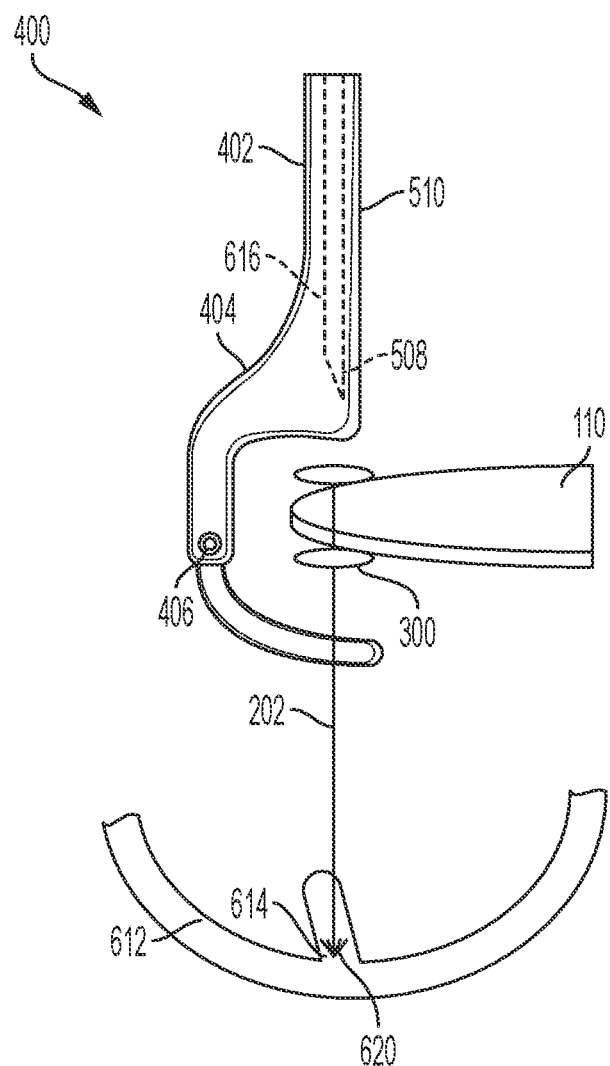
FIG. 8 shows an example chordae tendineae repair device in a fifth configuration in accordance with an embodiment.

FIG. 8 shows an example chordae tendineae repair device in a fifth configuration in accordance with an embodiment. As shown in FIG. 8, a delivery device 400 is shown with a capture device 404 having captured and clamped onto a leaflet 110. In addition, the delivery device 400 is in a configuration such that a needle 508 has been passed through the leaflet 110 and into a tissue wall 612 of a patient's heart, and retracted back through a channel 510 of the capture device 404. The flexible cord 202 has been anchored in the tissue wall 612 by an anchor 620.

To anchor the flexible cord 202 on the other end (a first or second end as compared to a first or second end at which the anchor 620 is attached to the flexible cord 202), a helical wire 300 may be attached to the flexible cord 202. The helical wire 300, in certain instances, is configured to attach to one of a first end and a second end of the flexible cord 202 and anchor the flexible cord 202 to the leaflet 110 of the heart valve. The helical wire 300 may be passed through (e.g., screwed) through the leaflet 110 and may be adjusted to vary the tension on the flexible cord 202 based on the depth at which the helical wire 300 is embedded in the leaflet. The helical wire 300 may also be deployed positioning and withdrawal of the needle 508 to expose a portion of the helical wire 300 on each side of the leaflet 110.

Figure 9:
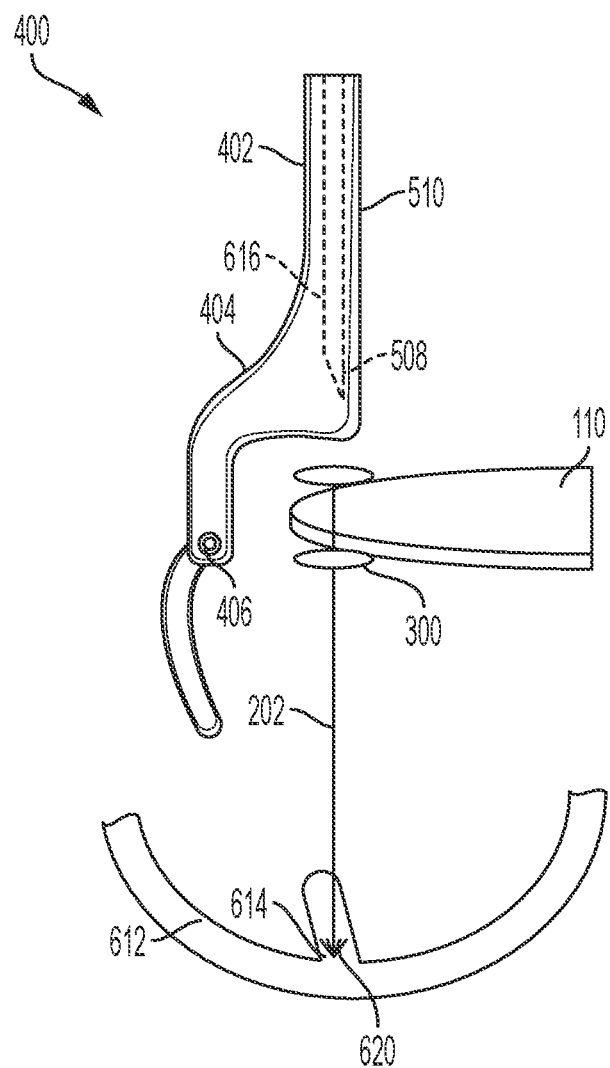
FIG. 9 shows an example chordae tendineae repair device in a sixth configuration in accordance with an embodiment.
Figure 10:
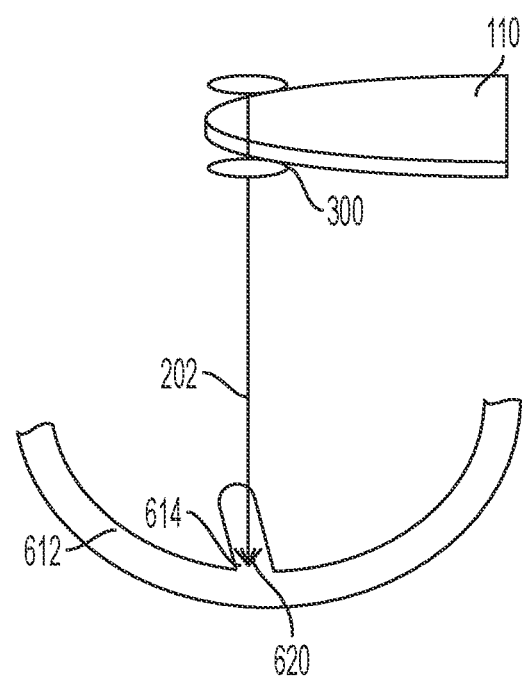
FIG. 10 shows an example chordae tendineae repair device in a seventh configuration in accordance with an embodiment.

After the helical wire 300 has been anchored or embedded in the leaflet 110, the flexible cord 202 is installed, the capture device 404 may be opened as shown in FIG. 9. A hinged portion 406 facilitates movement of the capture device 404 between open and closed (clamping) position. After the capture device 404 has been opened, the catheter 402 and the capture device 404 may be removed and the flexible cord 202 is installed as shown in FIG. 10.

Figure 11B:
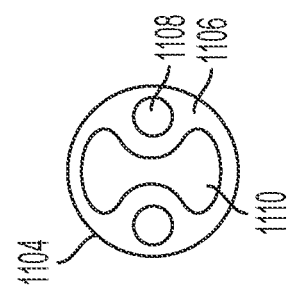
FIG. 11B shows an end view of a portion of the component of the example delivery apparatus, shown in FIG. 11A.
Figure 11A:
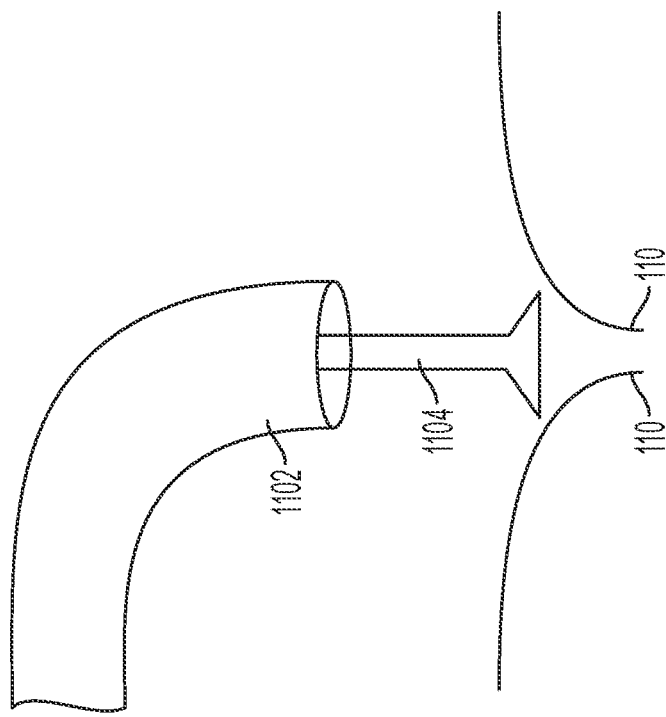
FIG. 11A shows an example component of a delivery apparatus in accordance with an embodiment.

FIG. 11A shows an example component of a delivery apparatus 1100 in accordance with an embodiment. The delivery apparatus 1100 includes a catheter 1102 that allows for transcatheter delivery of an artificial chordae tendineae repair device (e.g., flexible cord 202). The delivery apparatus 1100 may also include a suction device 1104 that is configured to capture a leaflet 110 for arrangement of the artificial chordae tendineae repair (or replacement) device through the leaflet 110 as described in detail above.

FIG. 11B shows an end view of a portion of the example delivery apparatus 1100, shown in FIG. 11A. The delivery apparatus 1100 includes a lumen 1106 through which a needle 1108 may be arranged. FIG. 11B also shows a suction area 1110.

Figure 12:
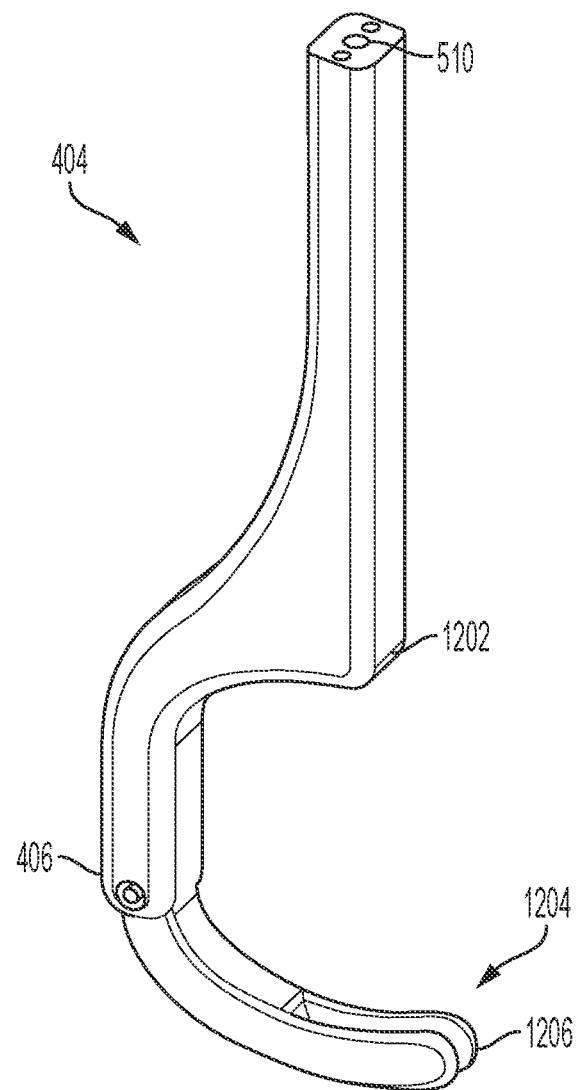
FIG. 12 shows another view of an example component the chordae tendineae repair device shown in FIGS. 4-10.

FIG. 12 shows another view of an example component of the chordae tendineae repair device shown in FIGS. 4-10. FIG. 12 shows a perspective view of a capture device 404 in accordance with various aspects of the present disclosure. As discussed in further detail above with reference to FIGS. 4-10, the capture device 404 includes a hinged portion 406 to facilitate movement of the capture device 404 between open and closed (clamping) position and a channel 510 through which, for example, a needle may be arranged.

The capture device 404 includes an upper portion 1202 and a lower portion 1204 that close together to grasp a leaflet. The lower portion 1204 may also include a groove or opening 1206 to facilitate arrangement of an anchor or helical wire and a flexible cord therethrough as discussed in detail above.

Figure 13:
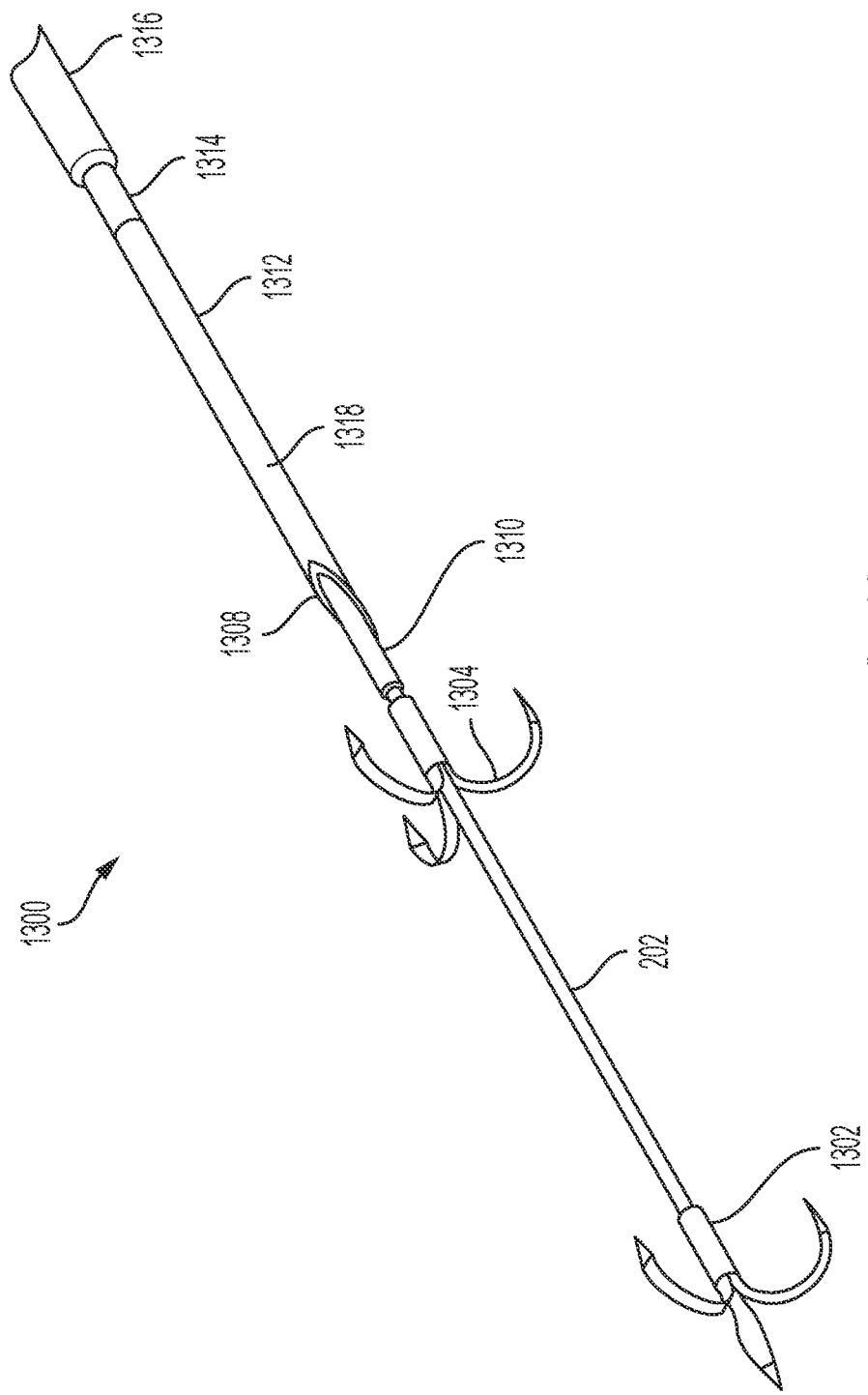
FIG. 13 shows an example tissue tethering device in accordance with an embodiment.

FIG. 13 shows an example tissue tethering device 1300 in accordance with an embodiment. The repair device includes a distal anchor 1302, a flexible cord 202, and a proximal anchor 1304. The distal anchor 1302 may be bonded to the flexible cord 202, and the proximal anchor 1304 may be slideably arranged with the flexible cord 202. The distal anchor 1302 may be arranged in one tissue and the proximal anchor 1304 may be arranged in another tissue, with the flexible cord 202 tethering the tissues together. The tethering device 1300 may be used in chordae tendineae repair as discussed in detail above.

The tethering device 1300 may also include a needle 1312 to puncture tissue in order to embed the distal anchor 1302 and the proximal anchor 1304. As shown, the needle 1312 includes a lumen 1308 through which the distal anchor 1302, the proximal anchor 1304, and the flexible cord 202 may pass. In certain instances, the proximal anchor 1304 slides over the flexible cord 202 until the proximal anchor 1304 exits the needle 1312 through the lumen 1308. In certain instances, the tethering device 1300 also includes an anchor pusher 1310 that can also be arranged through the lumen 1308 of the needle 1312. The anchor pusher 1310 facilitates embedding of the distal anchor 1302 and the proximal anchor 1304 in tissue, and also passing of the distal anchor 1302 and the proximal anchor 1304 the distal anchor 1302.

The tethering device 1300 may also include a fiber cutting feature 1318 that is configured to trim the flexible cord 202 as discussed in detail below. In certain instances, the tethering device 1300 also includes a pusher 1314 configured to facilitate movement of the needle 1312, and a catheter 1316 for transcatheter delivery.

In certain instances, the distal anchor 1302 and/or the proximal anchor 1304 may be replaced with a helical wire 300. In addition, the distal anchor 1302 and and/or the proximal anchor 1304 are structures that may be used as an anchor 620 as discussed in further detail above.

In certain instances, the catheter 1316 is a steerable catheter. In use, the catheter 1316 may be used to approximate a target tissue. The pusher 1314 may be advanced to puncture the tissue with the needle 1312. The catheter 1316 follows the needle 1312 through the tissue (e.g., a heart valve leaflet) to position the catheter 1316 at a second tissue target destination. The pusher 1314 is advanced such that the needle 1312 is in or through the second tissue. The anchor pusher 1310 is used to embed the distal anchor 1302 into the second tissue.

The catheter 1316 and the needle 1312 may be withdrawn to the first tissue with the flexible cord 202 being drawn out by withdrawal of the catheter 1316 and the needle 1312. The proximal anchor 1304 slides along the flexible cord during withdrawal of the catheter 1316 and the needle 1312 and embeds into the first tissue. Tension on the flexible cord 202 may be adjusted by adjusting the position of the proximal anchor 1304, thereby adjusting the length of the flexible cord 202 between the proximal anchor 1304 and the distal anchor 1302, and the proximal anchor 1304 may be deployed by pushing on the anchor pusher 1310. A free end, proximal of the embedded proximal anchor 1304, may be broken by the fiber cutting feature 1318 with the flexible cord 202 installed and tethering the first tissue and the second tissue.

Figure 14:
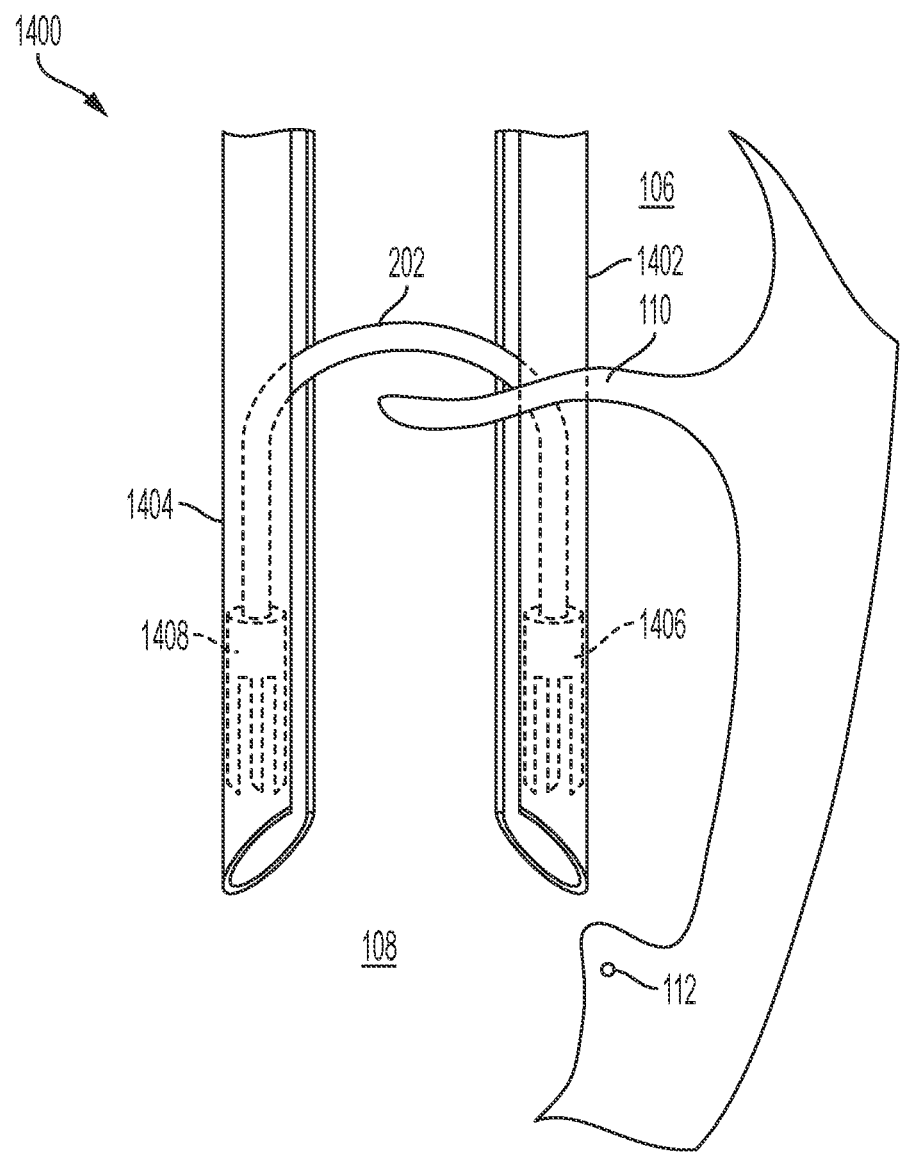
FIG. 14 shows another example chordae tendineae repair device in accordance with an embodiment.

FIG. 14 shows another example chordae tendineae repair device in accordance with an embodiment. As shown in FIG. 14, a delivery device 1400 is used to deliver a flexible cord 202. The flexible cord 202 is arranged through each of a first portion 1402 and a second portion 1404 of the delivery device 1400. In this manner, the flexible cord 202 can be arranged through a leaflet 110 without anchoring the flexible cord 202 into the leaflet using an anchor or other similar device. The first portion 1402 passes through the leaflet 110 for delivery of the flexible cord.

The flexible cord 202 may include anchors 1406, 1408 that can be embedded in tissue such as papillary muscles 112 in a left ventricle 108 on the other end with a loop or stitch formed by the flexible cord 202 arranged through the leaflet 110. The anchors 1406, 1408 are not anchored in the leaflet 110. Rather, the flexible cord 202 may be arranged on a surface of the leaflet 110 or through the leaflet 110 (forming a stitch in the leaflet 110). The delivery device 1400 passes through a left atrium 106 of a patient to be delivered to the leaflet 110 in the left ventricle 108. In this manner and for example, the flexible cord 202 is used for repair or replacement of chordae tendineae (not shown).

Figure 15:
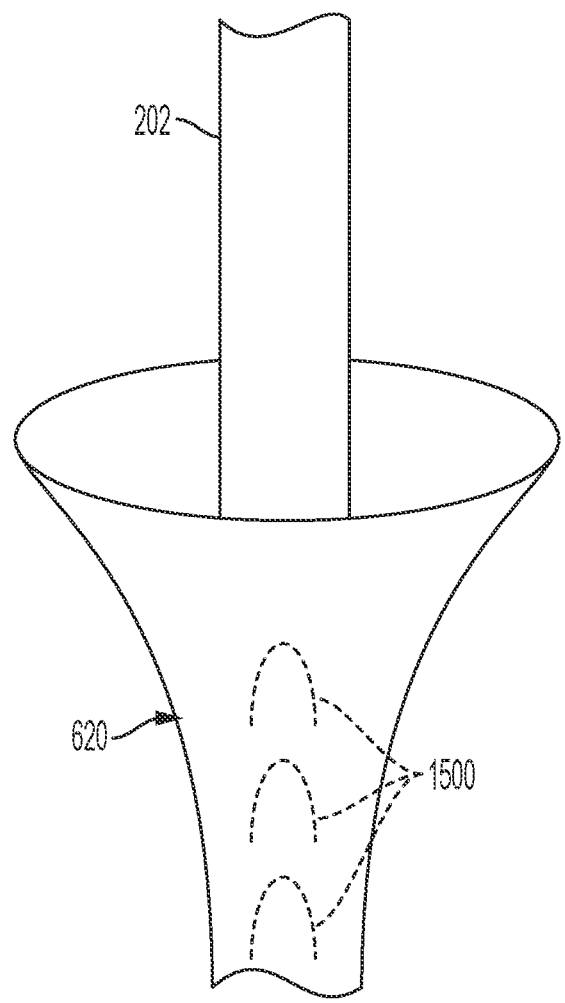
FIG. 15 shows an example attachment of a flexible cord with an anchor in accordance with an embodiment.

FIG. 15 shows an example attachment of a flexible cord 202 with an anchor 620 in accordance with an embodiment. The anchor 620 includes one or more grooves 1500 that are configured to grab and grip the flexible cord 202. The one or more grooves 1500 couple the flexible cord 202 with the anchor 620.

The one or more grooves 1500 facilitate adjusting of tension on the flexible cord 202, as described above with reference to FIGS. 4-10 and FIG. 13, by allowing the flexible cord 202 to pass through the anchor 620 in one direction. The one or more grooves 1500 grip the flexible cord 202 if the flexible cord 202 is withdrawn. The flexible cord 202 slides through the one or more grooves 1500 and is not able to be withdrawn in the opposite direction.

Figure 16:
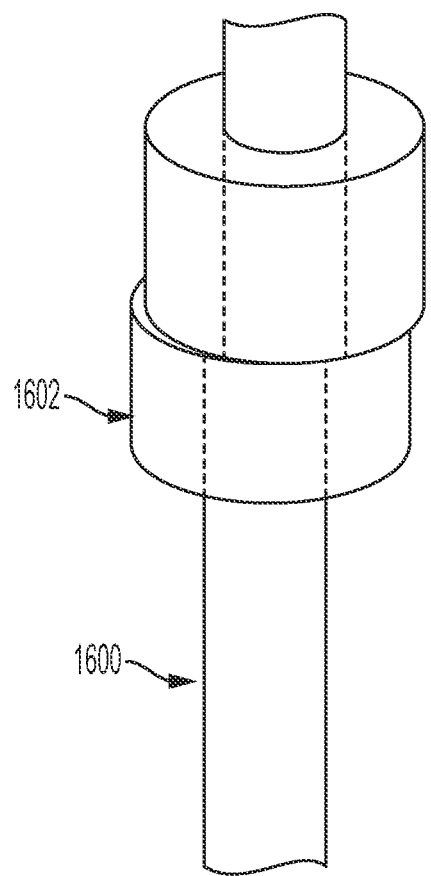
FIG. 16 shows an example hypotube in accordance with an embodiment.

FIG. 16 shows an example fixation of a cord 1600 with a split anchor 1602 in accordance with an embodiment. The split anchor 1602 includes a hypotube that facilitates delivery and removal of the split anchor 1602. The split anchor 1602 may be a bent cut-tube and may also be formed of heat treated Nitinol. The cord 1600 passes internally to the split anchor 1602 and is not able to be withdrawn once the hypotube is removed and the split anchor 1602 is no longer axially aligned.

Figure 17:
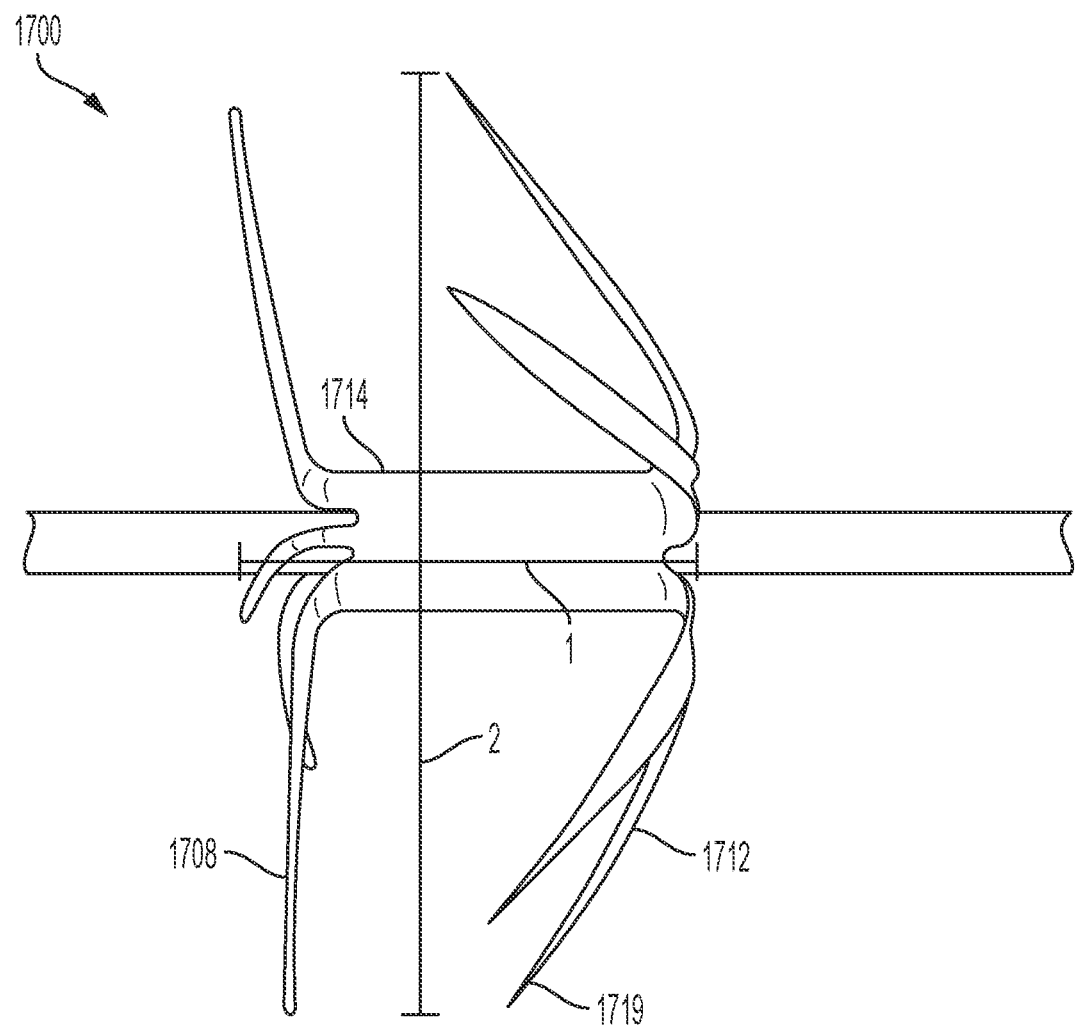
FIG. 17 shows an example anchor that may be used with a chordae tendineae repair device in accordance with an embodiment.

FIG. 17 shows an example anchor 1700 that may be used with a chordae tendineae repair device in accordance with an embodiment. The anchor 1700 may be coupled to one or both ends of a flexible cord 202 as discussed in detail above. The anchor 1700 may include anchor arms 1712 that may include a tissue-penetrating point 1719. In various embodiments, tissue-penetrating point 1719 is located at the end of a base portion 1718 of the anchor. Tissue-penetrating point 1719 can comprise a shape capable of penetrating tissue and securing anchor 1700 to the anatomy of the patient.

The anchor 1700 may also include flange element arms 1708 having a portion of the one or more flange element arms substantially everting to a position approximately 90 degrees from the central axis of the base portion 1718 of the anchor 110. The flange element arms 1708 may be configured to minimize or avoid penetration of tissue or a medical device or to avoid causing damage to tissue.

For further discussion of the anchor 1700, and other forms of the anchor 1700, reference may be made to U.S. Patent Publication No. 2014/0046347, which is incorporated herein by reference in its entirety for the specific purposes of teaching anchors for engaging tissue.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A device for chordae tendineae repair, the device comprising:
   a flexible cord having a first end and a second end;
   an anchor including one or more grooves configured to grip the flexible cord and facilitate tension adjustment of the flexible cord such that the flexible cord is able to slide through the one or more grooves in a first direction, and is not able to be withdrawn in a second, opposite direction;
   a helical wire configured to attach to one of the first end and the second end of the flexible cord and anchor the flexible cord to a leaflet of a heart valve; and
   a capture device having a channel and sidewalls forming a groove with a pathway between the sidewalls, the capture device being configured to clamp the leaflet of the heart valve, deliver the flexible cord through the channel to anchor the helical wire to the leaflet, and the flexible cord through the pathway, wherein the capture device includes a hinge configured to open and close the capture device.

2. The device of claim 1, wherein further comprising a puncture needle, and wherein the channel is configured to pass the puncture needle and the flexible cord therethrough, and the puncture needle is configured to puncture the leaflet while the capture device clamps the leaflet.

3. The device of claim 2, wherein the puncture needle includes a lumen configured to pass the flexible cord therethrough.

4. The device of claim 1, further wherein the anchor is configured to anchor the flexible cord in a tissue wall of a patient's heart.

5. The device of claim 1, further comprising a suction device configured to capture the leaflet for arrangement of the flexible cord through the leaflet.

6. The device of claim 1, wherein the capture device is arranged at a distal end of an elongate member, the capture device operable to clamp the leaflet of the heart valve.

7. The device of claim 6, further comprising a needle arranged in a channel of the elongate member and the capture device.

8. The device of claim 7, wherein the needle is operable to move between an extended configuration and a retracted configuration.

9. The device of claim 8, wherein, when the capture device is clamped onto the leaflet of the heart valve, the capture device is operable to align the leaflet of the heart valve for the needle to transition from the retracted configuration to the extended configuration in order to extend through the leaflet of the heart valve to create an opening in the leaflet of the heart valve.

10. A chordae tendineae repair device comprising:
    a flexible cord having a first end and a second end; and
    an anchor configured to attach to one of the first end and the second end of the flexible cord and anchor the flexible cord to a leaflet of a heart valve or to a tissue wall of the heart, the anchor including one or more grooves configured to grip the flexible cord and facilitate tension adjustment of the flexible cord such that the flexible cord is slidable through the one or more grooves in a first direction and is not slidable in a second, opposite direction;
    two or more pledgets coupled to the other of the first end and the second end of the flexible cord; and
    a capture device being configured to clamp the leaflet of the heart valve, wherein the capture device includes a hinge configured to open and close the capture device.

11. The device of claim 10, wherein the anchor is a helical wire and is wrapped with a film.

12. The device of claim 10, wherein the anchor is configured to protect or fill a puncture in the leaflet of the heart valve through which the anchor is arranged.

\* \* \* \* \*